(12) United States Patent
Sur

(10) Patent No.: US 11,998,687 B2
(45) Date of Patent: *Jun. 4, 2024

(54) MICROPUMP FOR AN AEROSOL DELIVERY DEVICE

(71) Applicant: RAI STRATEGIC HOLDINGS, INC., Winston-Salem, NC (US)

(72) Inventor: Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/077,571

(22) Filed: Dec. 8, 2022

(65) Prior Publication Data

US 2023/0097917 A1 Mar. 30, 2023

Related U.S. Application Data

(63) Continuation of application No. 16/203,069, filed on Nov. 28, 2018, now Pat. No. 11,547,816.

(51) Int. Cl.
*A61M 15/06* (2006.01)
*A24F 40/10* (2020.01)
(Continued)

(52) U.S. Cl.
CPC ............ *A61M 15/06* (2013.01); *A24F 40/10* (2020.01); *A24F 40/48* (2020.01); *A24F 40/50* (2020.01);
(Continued)

(58) Field of Classification Search
CPC .......... A24F 40/50; A24F 40/40; A24F 40/10; A24F 40/00
See application file for complete search history.

(56) References Cited

U.S. PATENT DOCUMENTS 2,057,353 A 10/1936 Whittemore, Jr.
2,104,266 A 1/1938 McCormick
(Continued)

FOREIGN PATENT DOCUMENTS

CN 1541577 11/2004
CN 2719043 8/2005
(Continued)

OTHER PUBLICATIONS

Feng, Z. et al., "Piezoelectric Micropump Driver Reference Design", Microchip Technology Incorporated, 2016, pp. 1-22.
(Continued)

*Primary Examiner* — Alex B Efta
(74) *Attorney, Agent, or Firm* — Womble Bond Dickinson (US) LLP

(57) ABSTRACT

An aerosol delivery device includes a housing enclosing a reservoir retaining an aerosol precursor composition. A first power-source terminal connects a power source to the aerosol delivery device. A heating element is configured to vaporize components of the aerosol precursor composition. A switch is coupled between the first power-source terminal and the heating element. A micro pump is arranged between the reservoir and the heating element to deliver aerosol precursor composition from the reservoir to the heating element. A driver circuit is coupled between the first power-source terminal and the micro pump, to drive the micro pump. A control component includes processing circuitry configured to switchably control the driver circuit to drive the micro pump, and switchably control the switch to connect the power source to the heating element and thereby power the heating element to vaporize components of the aerosol precursor composition.

28 Claims, 3 Drawing Sheets

(51) Int. Cl.
  *A24F 40/48* (2020.01)
  *A24F 40/50* (2020.01)
  *A61M 11/04* (2006.01)

(52) U.S. Cl.
  CPC ....... *A61M 11/042* (2014.02); *A61M 2205/13* (2013.01); *A61M 2205/3331* (2013.01); *A61M 2205/3653* (2013.01); *A61M 2205/8206* (2013.01)

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,060,671 A | 10/1991 | Counts et al. | |
| 5,093,894 A | 3/1992 | Deevi et al. | |
| 5,261,424 A | 11/1993 | Sprinkel, Jr. | |
| 5,388,574 A | 2/1995 | Ingebrethsen et al. | |
| 5,530,225 A | 6/1996 | Hajaligol | |
| 5,687,746 A | 11/1997 | Rose et al. | |
| 5,726,421 A | 3/1998 | Fleischhauer et al. | |
| 5,865,185 A | 2/1999 | Collins et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 11,547,816 B2 * | 1/2023 | Sur | A24F 40/10 |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056013 A1 | 3/2013 | Terry et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini | |
| 2014/0270729 A1 | 9/2014 | DePiano | |
| 2014/0270730 A1 | 9/2014 | DePiano | |
| 2014/0283855 A1 | 9/2014 | Hawes et al. | |
| 2014/0299137 A1 * | 10/2014 | Kieckbusch | A24F 40/51 131/328 |
| 2014/0334804 A1 | 11/2014 | Choi | |
| 2015/0173124 A1 * | 6/2015 | Qiu | A24F 40/60 131/328 |
| 2015/0216237 A1 * | 8/2015 | Wensley | A61M 11/001 131/273 |
| 2015/0333552 A1 * | 11/2015 | Alarcon | H02J 7/345 131/329 |
| 2016/0057811 A1 | 2/2016 | Alarcon et al. | |
| 2016/0213065 A1 * | 7/2016 | Wensley | H05B 3/16 |
| 2017/0043999 A1 * | 2/2017 | Murison | B65D 85/70 |
| 2017/0172212 A1 | 6/2017 | Phillips et al. | |
| 2017/0196270 A1 * | 7/2017 | Vick | H02J 7/0042 |
| 2018/0289076 A1 | 10/2018 | Manca et al. | |
| 2019/0045847 A1 | 2/2019 | Manca et al. | |
| 2019/0373679 A1 * | 12/2019 | Fu | A24F 7/00 |
| 2020/0060338 A1 * | 2/2020 | Danek | A61M 15/06 |

FOREIGN PATENT DOCUMENTS

| | | |
|---|---|---|
| CN | 201379072 | 1/2010 |
| EP | 0 295 122 | 12/1988 |
| EP | 0 845 220 | 6/1998 |
| EP | 1 618 803 | 1/2006 |
| GB | 2469850 | 11/2010 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2014/153515 | 9/2014 |
| WO | WO 2017/108429 | 6/2017 |

OTHER PUBLICATIONS

"Bartels Micropumps", Bartels Mikrotechnik GmbH, Mar. 2018, pp. 1-22.

International Search Report from corresponding International Appl. No. PCT/IB2019/060081, dated Mar. 11, 2020.

* cited by examiner

MICROPUMP FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking articles have been proposed through the years as improvements upon, or alternatives to, smoking products based upon combusting tobacco. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and PCT Pat. App. Pub. No. WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER© International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; MISTIC MENTHOL product by Mistic Ecigs; the VYPE product by CN Creative Ltd; IQOS™ by Philip Morris International; GLO™ by British American Tobacco; MARK TEN products by Nu Mark LLC; and the JUUL product by Juul Labs, Inc. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

However, it may be desirable to provide aerosol delivery devices with improved electronics such as may extend usability of the devices.

BRIEF SUMMARY

The present disclosure relates to aerosol delivery devices configured to produce aerosol and which aerosol delivery devices, in some implementations, may be referred to as electronic cigarettes or heat-not-burn cigarettes. The present disclosure includes, without limitation, the following example implementations.

Some example implementations provide an aerosol delivery device comprising a housing enclosing a reservoir configured to retain an aerosol precursor composition; a first power-source terminal configured to connect a power source to the aerosol delivery device; a heating element configured to convert electricity to heat and thereby vaporize components of the aerosol precursor composition; a switch coupled to and between the first power-source terminal and the heating element; a micro pump arranged to be operable between the reservoir and the heating element to deliver aerosol precursor composition from the reservoir to the heating element; a driver circuit coupled to and between the first power-source terminal and the micro pump, the driver circuit being configured to drive the micro pump; and a control component including processing circuitry configured to switchably control the driver circuit to drive the micro pump to deliver the aerosol precursor composition to the heating element, the processing circuitry also being configured to switchably control the switch to connect the power source to the heating element and thereby power the heating element to vaporize components of the aerosol precursor composition.

In some example implementations of the aerosol delivery device of any preceding example implementation, or any combination of any preceding example implementations, the driver circuit includes a boost converter configured to step up voltage from the power source to the micro pump to thereby power the micro pump.

In some example implementations of the aerosol delivery device of any preceding example implementation, or any combination of any preceding example implementations, the processing circuitry is configured to switchably control the switch to connect the power source to the heating element independent of the boost converter.

In some example implementations of the aerosol delivery device of any preceding example implementation, or any combination of any preceding example implementations, the aerosol delivery device further comprises a sensor configured to produce a measurement of pressure caused by airflow through at least a portion of the housing, and convert the measurement of pressure to a corresponding electrical signal, wherein the processing circuitry being configured to switchably control the switch to connect the power source to the heating element includes being configured to receive the corresponding electrical signal and in response control the switch to connect the power source to the heating element.

In some example implementations of the aerosol delivery device of any preceding example implementation, or any combination of any preceding example implementations, the switch is a high-side load switch, and the processing circuitry being configured to switchably control the switch to connect the power source to the heating element includes being configured to switchably control the high-side load switch to connect the power source to the heating element.

In some example implementations of the aerosol delivery device of any preceding example implementation, or any combination of any preceding example implementations, the micro pump is a mechanical micro pump, and the mechanical micro pump is a diaphragm micro pump or a peristaltic micro pump.

In some example implementations of the aerosol delivery device of any preceding example implementation, or any combination of any preceding example implementations, the micro pump is a non-mechanical micro pump, and the non-mechanical micro pump is a valveless micro pump, a capillary micro pump or a chemically-powered pump.

In some example implementations of the aerosol delivery device of any preceding example implementation, or any combination of any preceding example implementations, the aerosol delivery device comprises a liquid transport element between and fluidly connecting the micro pump and the heating element.

In some example implementations of the aerosol delivery device of any preceding example implementation, or any combination of any preceding example implementations, the processing circuitry is configured to switchably drive the micro pump to deliver the aerosol precursor composition once for a predetermined period per $n>1$ cycles of the power source being switchably connected to the heating element via the switch.

In some example implementations of the aerosol delivery device of any preceding example implementation, or any combination of any preceding example implementations, the processing circuitry being configured to control the driver circuit includes being configured to switchably control the driver circuit to drive the micro pump at an adjustable frequency that is directly related to a volume flow rate of aerosol precursor composition through the micro pump.

In some example implementations of the aerosol delivery device of any preceding example implementation, or any combination of any preceding example implementations, the driver circuit includes a boost converter configured to step up voltage from the power source to the micro pump to thereby power the micro pump, and the processing circuitry being configured to switchably control the driver circuit includes being configured to switchably control the boost converter to step up the voltage from the power source to an adjustable higher voltage that is directly related to a volume flow rate of aerosol precursor composition through the micro pump.

In some example implementations of the aerosol delivery device of any preceding example implementation, or any combination of any preceding example implementations, the driver circuit includes a boost converter configured to step up voltage from the power source to the micro pump to thereby power the micro pump, the control component is configured to receive an indication of a user-selected amount of aerosol precursor composition, and the processing circuitry being configured to switchably control the driver circuit includes being configured to switchably control the driver circuit to drive the micro pump at an adjustable frequency, or switchably control the boost converter to step up the voltage from the power source to an adjustable higher voltage, that causes the micro pump to deliver the selectable amount of aerosol precursor composition to the heating element.

In some example implementations of the aerosol delivery device of any preceding example implementation, or any combination of any preceding example implementations, the control component includes a communication interface coupled to the processing circuitry and configured to enable the aerosol delivery device to establish wireless communication with a computing device configured to provide the indication of the user-selected amount of aerosol precursor composition.

In some example implementations of the aerosol delivery device of any preceding example implementation, or any combination of any preceding example implementations, the aerosol precursor composition comprises glycerin and nicotine.

In some example implementations of the aerosol delivery device of any preceding example implementation, or any combination of any preceding example implementations, the first power-source terminal and a second power-source terminal, the micro pump, the driver circuit and the control component are contained within the housing.

In some example implementations of the aerosol delivery device of any preceding example implementation, or any combination of any preceding example implementations, the housing is of a cartridge, the aerosol delivery device further comprises a control body with a second housing, and the first power-source terminal and a second power-source terminal, the micro pump, the driver circuit and the control component are contained within the second housing.

Some example implementations provide a control body for an aerosol delivery device, the control body comprising a housing enclosing a reservoir configured to retain an aerosol precursor composition; a first power-source terminal configured to connect a power source to the control body; heating-element terminals configured to connect a heating element to the control body, the heating element being configured to convert electricity to heat and thereby vaporize components of the aerosol precursor composition; a switch coupled to and between the first power-source terminal and the heating element; a micro-pump terminal configured to connect a micro pump to the control body, the micro pump being arranged to be operable between the reservoir and the heating element to deliver aerosol precursor composition from the reservoir to the heating element; a driver circuit coupled to and between the first terminal and the micro pump, the driver circuit being configured to drive the micro pump; and a control component including processing circuitry configured to switchably control the driver circuit to drive the micro pump to deliver the aerosol precursor composition to the heating element, the processing circuitry also being configured to switchably control the switch to connect the power source to the heating element and thereby power the heating element to vaporize components of the aerosol precursor composition.

In some example implementations of the control body of any preceding example implementation, or any combination of any preceding example implementations, the driver circuit includes a boost converter configured to step up voltage from the power source to the micro pump to thereby power the micro pump.

In some example implementations of the control body of any preceding example implementation, or any combination of any preceding example implementations, the processing circuitry is configured to switchably control the switch to connect the power source to the heating element independent of the boost converter.

In some example implementations of the control body of any preceding example implementation, or any combination of any preceding example implementations, the control body comprises a sensor configured to produce a measurement of pressure caused by airflow through at least a portion of the housing, and convert the measurement of pressure to a corresponding electrical signal, and the processing circuitry being configured to switchably control the switch to connect the power source to the heating element includes being configured to receive the corresponding electrical signal and in response control the switch to connect the power source to the heating element.

In some example implementations of the control body of any preceding example implementation, or any combination of any preceding example implementations, the switch is a high-side load switch, and the processing circuitry being configured to switchably control the switch to connect the power source to the heating element includes being configured to switchably control the high-side load switch to connect the power source to the heating element.

In some example implementations of the control body of any preceding example implementation, or any combination of any preceding example implementations, the micro pump is a mechanical micro pump, and the mechanical micro pump is a diaphragm micro pump or a peristaltic micro pump.

In some example implementations of the control body of any preceding example implementation, or any combination of any preceding example implementations, the micro pump is a non-mechanical micro pump, and the non-mechanical micro pump is a valveless micro pump, a capillary micro pump or a chemically-powered pump.

In some example implementations of the control body of any preceding example implementation, or any combination of any preceding example implementations, the processing circuitry is configured to switchably drive the micro pump to deliver the aerosol precursor composition once for a predetermined period per $n>1$ cycles of the power source being switchably connected to the heating element via the switch.

In some example implementations of the control body of any preceding example implementation, or any combination of any preceding example implementations, the processing circuitry being configured to switchably control the driver circuit includes being configured to switchably control the driver circuit to drive the micro pump at an adjustable frequency that is directly related to a volume flow rate of aerosol precursor composition through the micro pump.

In some example implementations of the control body of any preceding example implementation, or any combination of any preceding example implementations, the driver circuit includes a boost converter configured to step up voltage from the power source to the micro pump to thereby power the micro pump, and the processing circuitry being configured to switchably control the driver circuit includes being configured to switchably control the boost converter to step up the voltage from the power source to an adjustable higher voltage that is directly related to a volume flow rate of aerosol precursor composition through the micro pump.

In some example implementations of the control body of any preceding example implementation, or any combination of any preceding example implementations, the driver circuit includes a boost converter configured to step up voltage from the power source to the micro pump to thereby power the micro pump, the control component is configured to receive an indication of a user-selected amount of aerosol precursor composition, and the processing circuitry being configured to switchably control the driver circuit includes being configured to switchably control the driver circuit to drive the micro pump at an adjustable frequency, or switchably control the boost converter to step up the voltage from the power source to an adjustable higher voltage, that causes the micro pump to deliver the selectable amount of aerosol precursor composition to the heating element.

In some example implementations of the control body of any preceding example implementation, or any combination of any preceding example implementations, the control component includes a communication interface coupled to the processing circuitry and configured to enable the control body to establish wireless communication with a computing device configured to provide the indication of the user-selected amount of aerosol precursor composition.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1:
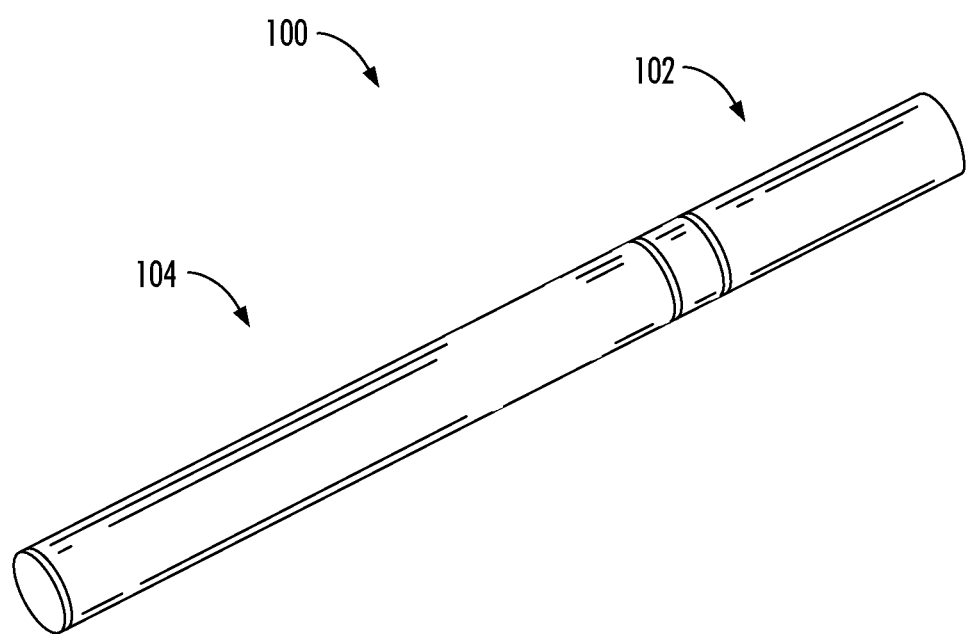
Figure 2:
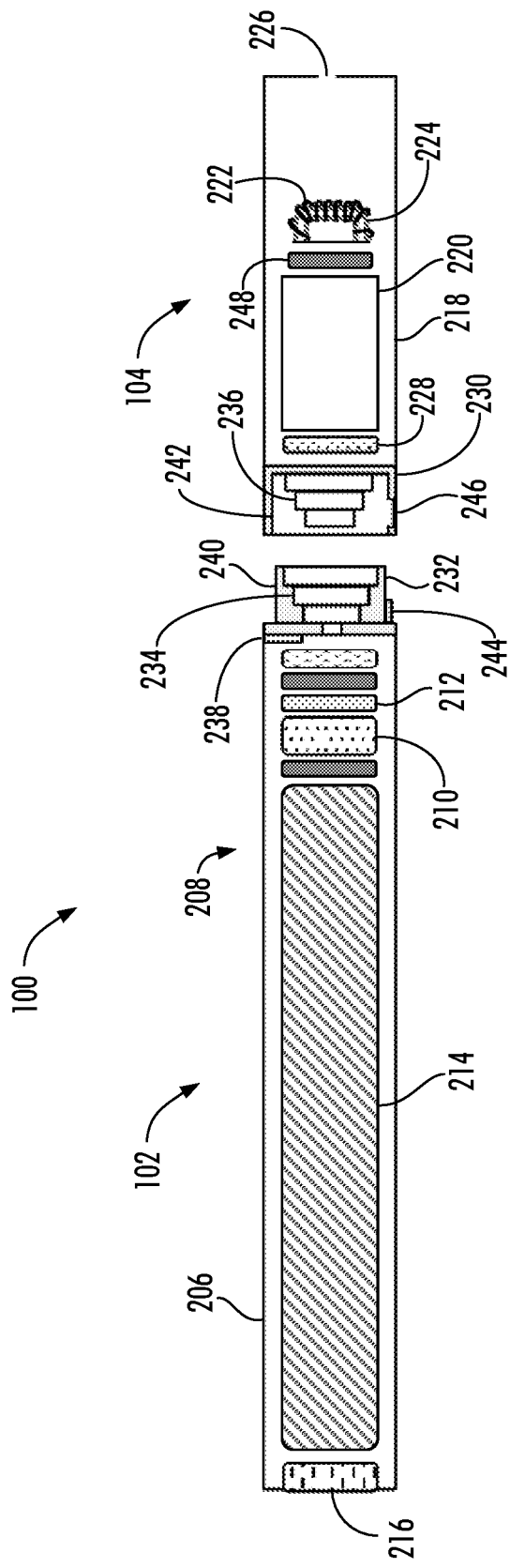
Figure 3:
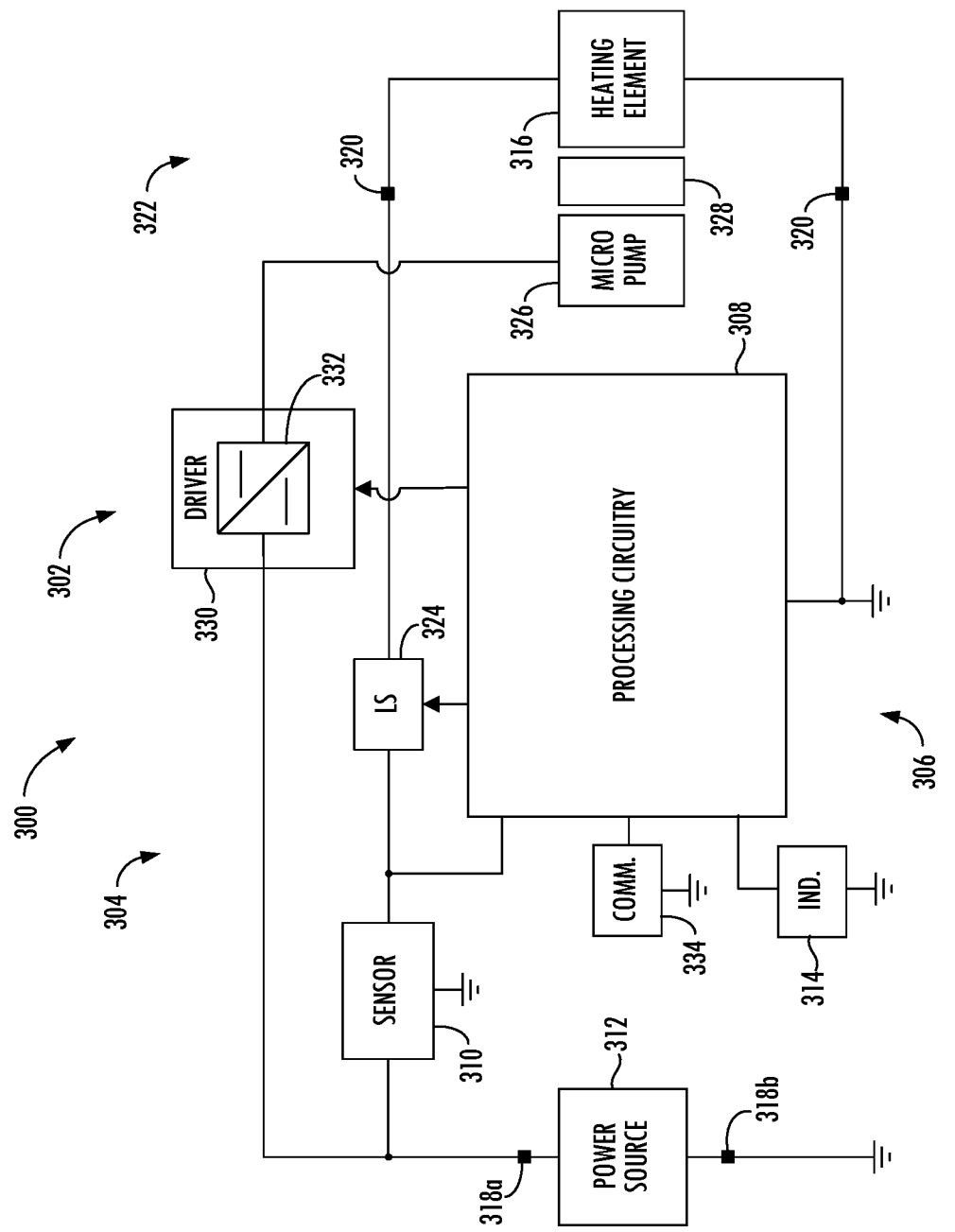

Having thus described aspects of the disclosure in the foregoing general terms, reference will now be made to the accompanying figures, which are not necessarily drawn to scale, and wherein:

FIG. 1 illustrates a perspective view of an aerosol delivery device including a cartridge and a control body that are coupled to one another, according to an example implementation of the present disclosure;

FIG. 2 is a partially cut-away view of the aerosol delivery device of FIG. 1 in which the cartridge and control body are decoupled from one another, according to an example implementation; and FIG. 3 is a circuit diagram of an aerosol delivery device that may be or incorporate functionality of the aerosol delivery device of FIGS. 1 and 2, according to various example implementations.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that component for inhalation of aerosol produced by that component, take or draw puffs at selected intervals of time, and the like.

While the systems are generally described herein in terms of implementations associated with aerosol delivery devices such as so-called "e-cigarettes," "tobacco heating products" and the like, it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer housing, which may be referred to as a body or shell. The overall design of the housing can vary, and the format or configuration of the housing that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated housing that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery, rechargeable supercapacitor, solid-state battery (SSB), thin-film SSB, and/or lithium ion or hybrid lithium ion supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices. It will be appreciated that alternative non-tubular housing form factors can also be used, including, for example, device housings having a shape and size generally approximating a pack of cigarettes and form factors such as used on the GLO™ by British American Tobacco and IQOS™ by Philip Morris International, Inc.

As will be discussed in more detail below, aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the aerosol delivery device), a heating element (e.g., an electrical resistance heating element or other component and/or an inductive coil or other associated components and/or one or more radiant heating elements), and an aerosol precursor composition (e.g., a solid tobacco material, a semi-solid tobacco material, or a liquid aerosol precursor composition) capable of yielding an aerosol upon application of sufficient heat, and a mouth end region or tip to allow drawing upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element may be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery, supercapacitor, SSB or other power source to provide current flow sufficient to provide various functionalities to the aerosol delivery device, such as powering of a heating element, powering of control systems, powering of indicators, and the like. The power source can take on various implementations. Preferably, the power source is able to deliver sufficient power to rapidly activate the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As described hereinafter, the present disclosure relates to aerosol delivery devices. Aerosol delivery devices may be configured to heat an aerosol precursor composition (sometimes referred to as an inhalable substance medium) to produce an aerosol (an inhalable substance). The aerosol precursor composition may comprise one or more of a solid tobacco material, a semi-solid tobacco material, or a liquid aerosol precursor composition. In some implementations, the aerosol delivery devices may be configured to heat and produce an aerosol from a fluid aerosol precursor composition (e.g., a liquid aerosol precursor composition). Such aerosol delivery devices may include so-called electronic cigarettes. In other implementations, the aerosol delivery devices may comprise heat-not-burn devices.

Liquid aerosol precursor composition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. In some examples, the aerosol precursor composition comprises glycerin and nicotine. It may also contain, in some examples, high-content water such as 90% water with added flavorants, or 90% water-based flavorants and a less percentage of nicotine.

Some liquid aerosol precursor compositions that may be used in conjunction with various implementations may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al., U.S. Pat. No. 9,254,002 to Chong et al., and U.S. Pat. App. Pub. Nos. 2013/0008457 to Zheng et al., 2015/0020823 to Lipowicz et al., and 2015/0020830 to Koller, as well as PCT Pat. App. Pub. No. WO 2014/182736 to Bowen et al., and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al, U.S. Pat. No. 8,627,828 to Strickland et al., and U.S. Pat. No. 9,307,787 to Sun et al., as well as U.S. Pat. App. Pub. Nos. 2010/0018539 to Brinkley et al., and PCT Pat. App. Pub. No. WO 97/06786 to Johnson et al., all of which are incorporated by reference herein.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al., U.S. Pat. No. 8,464,726 to Sebastian et al., U.S. Pat. App. Pub. No. 2015/0083150 to Conner et al., U.S. Pat. App. Pub. No. 2015/0157052 to Ademe et al., and U.S. Pat. App. Pub. No. 2017/0000188 to Nordskog et al., all of which are incorporated by reference herein. Further representative types of solid and semi-solid aerosol precursor compositions and arrangements include those found in the NEOSTIKS™ consumable aerosol source members for the GLO™ product by British American Tobacco and in the HEETS™ consumable aerosol source members for the IQOS™ product by Philip Morris International, Inc.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

Tobacco materials useful in the present disclosure can vary and may include, for example, flue-cured tobacco, burley tobacco, Oriental tobacco or Maryland tobacco, dark tobacco, dark-fired tobacco and *Rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S. Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., and U.S. Pat. No. 7,017,585 to Li et al., U.S. Pat. No. 7,025,066 to Lawson et al., U.S. Pat. App. Pub. No. 2004/0255965 to Perfetti et al., PCT Pat. App. Pub. No. WO 02/37990 to Bereman, and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No.

4,807,809 to Pryor et al., U.S. Pat. No. 4,889,143 to Pryor et al. and U.S. Pat. No. 5,025,814 to Raker, the disclosures of which are incorporated herein by reference. For further information regarding suitable aerosol precursor composition, see U.S. patent application Ser. No. 15/916,834 to Sur et al., filed Mar. 9, 2018, which is incorporated herein by reference.

Regardless of the type of aerosol precursor composition heated, aerosol delivery devices may include a heating element configured to heat the aerosol precursor composition. In some implementations, the heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially located or received within the induction transmitter and may include a conductive material (e.g., ferromagnetic material or an aluminum coated material). By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al., U.S. Pat. App. Pub. No. 2017/0202266 to Sur et al., U.S. patent application Ser. No. 15/352,153 to Sur et al., filed Nov. 15, 2016, U.S. patent application Ser. No. 15/799,365 to Sebastian et al., filed Oct. 31, 2017, and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety forms, such as in the form of a foil, a foam, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al.

In some implementations aerosol delivery devices may include a control body and a cartridge in the case of so-called electronic cigarettes, or a control body and an aerosol source member in the case of heat-not-burn devices. In the case of either electronic cigarettes or heat-not-burn devices, the control body may be reusable, whereas the cartridge/aerosol source member may be configured for a limited number of uses and/or configured to be disposable. The cartridge/aerosol source member may include the aerosol precursor composition. In order to heat the aerosol precursor composition, the heating element may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device.

In various implementations, the aerosol delivery device according to the present disclosure may have a variety of overall shapes, including, but not limited to an overall shape that may be defined as being substantially rod-like or substantially tubular shaped or substantially cylindrically shaped. In the implementations shown in and described with reference to the accompanying figures, the aerosol delivery device has a substantially round cross-section; however, other cross-sectional shapes (e.g., oval, square, rectangle, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, SSB, thin-film SSB, rechargeable supercapacitor, lithium ion or hybrid lithium ion supercapacitor, or the like. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series.

In some examples, then, the power source may be connected to and thereby combined with any type of recharging technology. Examples of suitable chargers include chargers that simply supply constant or pulsed direct current (DC) power to the power source, fast chargers that add control circuitry, three-stage chargers, induction-powered chargers, smart chargers, motion-powered chargers, pulsed chargers, solar chargers, USB-based chargers and the like. In some examples, the charger includes a power adapter and any suitable charge circuitry. In other examples, the charger includes the power adapter and the control body is equipped with charge circuitry. In these other examples, the charger may at times be simply referred to as a power adapter.

The control body may include any of a number of different terminals, electrical connectors or the like to connect to a suitable charger, and in some examples, to connect to other peripherals for communication. More specific suitable examples include direct current (DC) connectors such as cylindrical connectors, cigarette lighter connectors and USB connectors including those specified by USB 1.x (e.g., Type A, Type B), USB 2.0 and its updates and additions (e.g., Mini A, Mini B, Mini AB, Micro A, Micro B, Micro AB) and USB 3.x (e.g., Type A, Type B, Micro B, Micro AB, Type C), proprietary connectors such as Apple's Lightning connector, and the like. The control body may directly connect with the charger or other peripheral, or the two may connect via an appropriate cable that also has suitable connectors. In examples in which the two are connected by cable, the control body and charger or other peripheral may have the same or different type of connector with the cable having the one type of connector or both types of connectors.

In examples involving induction-powered charging, the aerosol delivery device may be equipped with inductive wireless charging technology and include an induction receiver to connect with a wireless charger, charging pad or the like that includes an induction transmitter and uses inductive wireless charging (including for example, wireless charging according to the Qi wireless charging standard from the Wireless Power Consortium (WPC)). Or the power source may be recharged from a wireless radio frequency (RF) based charger. An example of an inductive wireless charging system is described in U.S. Pat. App. Pub. No. 2017/0112196 to Sur et al., which is incorporated herein by reference in its entirety. Further, in some implementations in the case of an electronic cigarette, the cartridge may comprise a single-use cartridge, as disclosed in U.S. Pat. No. 8,910,639 to Chang et al., which is incorporated herein by reference.

One or more connections may be employed to connect the power source to a recharging technology, and some may involve a charging case, cradle, dock, sleeve or the like. More specifically, for example, the control body may be configured to engage a cradle that includes a USB connector to connect to a power supply. Or in another example, the control body may be configured to fit within and engage a sleeve that includes a USB connector to connect to a power supply. In these and similar examples, the USB connector may connect directly to the power source, or the USB connector may connect to the power source via a suitable power adapter.

Examples of power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

An input element may be included with the aerosol delivery device (and may replace or supplement a flow sensor). The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. As still a further example, a capacitive sensor may be implemented on the aerosol delivery device to enable a user to provide input, such as by touching a surface of the device on which the capacitive sensor is implemented. In another example, a sensor capable of detecting a motion associated with the device (e.g., accelerometer, gyroscope, photoelectric proximity sensor, etc.) may be implemented on the aerosol delivery device to enable a user to provide input. Examples of suitable sensors are described in U.S. Pat. App. Pub. No. 2018/0132528 to Sur et al., and U.S. Pat. App. Pub. No. 2016/0158782 to Henry et al., which are incorporated herein by reference.

As indicated above, the aerosol delivery device may include various electronics such as at least one control component. A suitable control component may include a number of electronic components, and in some examples may be formed of a circuit board such as a printed circuit board (PCB). In some examples, the electronic components include processing circuitry configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

In some examples, the control component may include one or more input/output peripherals, which may be coupled to or integrated with the processing circuitry. More particularly, the control component may include a communication interface to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

Still further components can be utilized in the aerosol delivery device of the present disclosure. One example of a suitable component is an indicator such as light-emitting diodes (LEDs), quantum dot-based LEDs or the like, which may be illuminated with use of the aerosol delivery device. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Other indices of operation are also encompassed by the present disclosure. For example, visual indicators of operation also include changes in light color or intensity to show progression of the smoking experience. Tactile (haptic) indicators of operation and sound (audio) indicators of operation similarly are encompassed by the disclosure. Moreover, combinations of such indicators of operation also are suitable to be used in a single smoking article. According to another aspect, the aerosol delivery device may include one or more indicators or indicia, such as, for example, a display configured to provide information corresponding to the operation of the smoking article such as, for example, the amount of power remaining in the power source, progression of the smoking experience, indication corresponding to activating a heat source, and/or the like.

Yet other components are also contemplated. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference.

Further examples of components related to electronic aerosol delivery articles and disclosing materials or components that may be used in the present article include U.S. Pat. No. 4,735,217 to Gerth et al., U.S. Pat. No. 5,249,586 to Morgan et al., U.S. Pat. No. 5,666,977 to Higgins et al., U.S. Pat. No. 6,053,176 to Adams et al., U.S. Pat. No. 6,164,287 to White, U.S. Pat. No. 6,196,218 to Voges, U.S. Pat. No. 6,810,883 to Felter et al., U.S. Pat. No. 6,854,461 to Nichols, U.S. Pat. No. 7,832,410 to Hon, U.S. Pat. No. 7,513,253 to 5 Kobayashi, U.S. Pat. No. 7,896,006 to Hamano, U.S. Pat. No. 6,772,756 to Shayan, U.S. Pat. Nos. 8,156,944 and 8,375,957 to Hon, U.S. Pat. No. 8,794,231 to Thorens et al., U.S. Pat. No. 8,851,083 to Oglesby et al., U.S. Pat. Nos. 8,915,254 and 8,925,555 to Monsees et al., U.S. Pat. No. 9,220,302 to DePiano et al., U.S. Pat. App. Pub. Nos. 2006/0196518 and 2009/0188490 to Hon, U.S. Pat. App. Pub. No. 2010/0024834 to Oglesby et al., U.S. Pat. App. Pub. No. 2010/0307518 to Wang, PCT Pat. App. Pub. No. WO 2010/091593 to Hon, and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

FIGS. 1 and 2 illustrate implementations of an aerosol delivery device including a control body and a cartridge in the case of an electronic cigarette. More specifically, FIGS. 1 and 2 illustrate an aerosol delivery device 100 according to an example implementation of the present disclosure. As indicated, the aerosol delivery device may include a control body 102 and a cartridge 104. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration.

The control body 102 and the cartridge 104 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. As shown, for example, the control body can be formed of a housing 206 (sometimes referred to as a control body shell) that can include electronic components 208 such as a control component 210 (e.g., processing circuitry, etc.), a flow sensor 212, a power source 214 (e.g., battery, supercapacitor), and an indicator 216 (e.g., LED, quantum dot-based LED), and such components can be variably aligned. The power source may be rechargeable, and the control body may include charging circuitry coupled to and configured to controllably charge the power source.

The cartridge 104 can be formed of a housing 218 (sometimes referred to as the cartridge shell) enclosing a reservoir 220 configured to retain the aerosol precursor composition, and including a heating element 222 (sometimes referred to as a heater). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 220 may be in fluid communication with a liquid transport element 224 adapted to wick or otherwise transport an aerosol precursor composition stored in the reservoir housing to the heating element 222. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 222. The heating element in these examples may be a resistive heating element such as a wire coil, micro heater or the like. Example materials from which the heating element may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). The heating element may be resistive heating element or a heating element configured to generate heat through induction. The heating element may be coated by heat conductive ceramics such as aluminum nitride, silicon carbide, beryllium oxide, alumina, silicon nitride, or their composites. Example implementations of heating elements useful in aerosol delivery devices according to the present disclosure are further described below, and can be incorporated into devices such as those described herein.

An opening 226 may be present in the housing 218 (e.g., at the mouth end) to allow for egress of formed aerosol from the cartridge 104.

The cartridge 104 also may include one or more electronic components 228, which may include an integrated circuit, a memory component (e.g., EEPROM, flash memory), a sensor, or the like. The electronic components may be adapted to communicate with the control component 210 and/or with an external device by wired or wireless means. The electronic components may be positioned anywhere within the cartridge or a base 230 thereof.

Although the control component 210 and the flow sensor 212 are illustrated separately, it is understood that various electronic components 208 including the control component and the flow sensor may be combined on a circuit board (e.g., PCB) that supports and electrically connects the electronic components. Further, the circuit board may be positioned horizontally relative the illustration of FIG. 1 in that the circuit board can be lengthwise parallel to the central axis of the control body. In some examples, the air flow sensor may comprise its own circuit board or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 102 and the cartridge 104 may include components adapted to facilitate a fluid engagement therebetween. As illustrated in FIG. 2, the control body can include a coupler 232 having a cavity 234 therein. The base 230 of the cartridge can be adapted to engage the coupler and can include a projection 236 adapted to fit within the cavity. Such engagement can facilitate a stable connection between the control body and the cartridge as well as establish an electrical connection between the power source 214 and control component 210 in the control body and the heating element 222 in the cartridge. Further, the housing 206 can include an air intake 238, which may be a notch in the housing where it connects to the coupler that allows for passage of ambient air around the coupler and into the housing where it then passes through the cavity 234 of the coupler and into the cartridge through the projection 236.

A coupler and a base useful according to the present disclosure are described in U.S. Pat. App. Pub. No. 2014/0261495 to Novak et al., which is incorporated herein by reference. For example, the coupler 232 as seen in FIG. 2 may define an outer periphery 240 configured to mate with an inner periphery 242 of the base 230. In one example the inner periphery of the base may define a radius that is substantially equal to, or slightly greater than, a radius of the outer periphery of the coupler. Further, the coupler may define one or more protrusions 244 at the outer periphery configured to engage one or more recesses 246 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 220 illustrated in FIG. 2 can be a container or can be a fibrous reservoir, as presently described. For example, the reservoir can comprise one or more layers of nonwoven fibers substantially formed into the shape of a tube encircling the interior of the housing 218, in this example. An aerosol precursor composition can be retained in the reservoir. Liquid components, for example, can be sorptively retained by the reservoir. The reservoir can be in fluid connection with the liquid transport element 224. The liquid transport element can transport the aerosol precursor composition stored in the reservoir via capillary action—or via micro pump as described below—to the heating element 222 that is in the form of a metal wire coil in this example. As such, the heating element is in a heating arrangement with the liquid transport element.

In some examples, a microfluidic chip may be embedded in the reservoir 220, and the amount and/or mass of aerosol precursor composition delivered from the reservoir may be controlled by a micro pump 248, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 212, and the heating element 222 is activated to vaporize components of the aerosol precursor composition. Drawing upon the mouth end of the aerosol delivery device causes ambient air to enter the air intake 238 and pass through the cavity 234 in the coupler 232 and the central opening in the projection 236 of the base 230. In the cartridge 104, the drawn air combines with the formed vapor to form an aerosol. The aerosol is whisked, aspirated or otherwise drawn away from the heating element and out the opening 226 in the mouth end of the aerosol delivery device.

For further detail regarding implementations of an aerosol delivery device including a control body and a cartridge in the case of an electronic cigarette, see the above-cited U.S. patent application Ser. No. 15/836,086 to Sur, and U.S. patent application Ser. No. 15/916,834 to Sur et al., as well as U.S. patent application Ser. No. 15/916,696 to Sur, filed Mar. 9, 2018, which is also incorporated herein by reference. In other implementations, the aerosol delivery device includes a control body and an aerosol source member in the case of a heat-not-burn device. Further details of at least some of these implementations may be found in the above-cited U.S. patent application Ser. No. 15/916,834 to Sur et al., U.S. patent application Ser. No. 15/916,696 to Sur, and U.S. patent application Ser. No. 15/836,086 to Sur.

As described above, the aerosol delivery device of example implementations may include various electronic components in the context of either an electronic cigarette or a heat-not-burn device, or even in the case of a device that includes the functionality of both. FIG. 3 is a circuit diagram of an aerosol delivery device 300 that may be or incorporate functionality of at least aerosol delivery device 100, according to various example implementations of the present disclosure. As shown, the aerosol delivery device includes a control body 302 with electronic components 304 including a control component 306 (with processing circuitry 308), a sensor 310, a power source 312 and an indicator 314 that may correspond to or include functionality of respective ones of the control body 102, electronic components 208, control component 210, flow sensor 212, power source 214 and indicator 216. The aerosol delivery device also includes a heating element 316 that may correspond to or include functionality of heating element 222. The heating element is configured to convert electricity to heat and thereby vaporize components of aerosol precursor composition.

The aerosol delivery device 300 may include a first power-source terminal 318a and a second power-source terminal 318b (e.g., respectively a positive power-source terminal and a negative power-source terminal) configured to connect the power source 310 to the aerosol delivery device. And in some examples such as those in which the aerosol delivery device 300 is or incorporates the functionality of aerosol delivery device 100, the aerosol delivery device 300 (or more specifically its control body 302) may include terminals 320 configured to connect the heating element 314 to the control body.

As described in greater detail above with respect to flow sensor 212, in some examples, the sensor 310 is configured to produce a measurement of pressure caused by airflow through at least a portion of the housing of the aerosol delivery device 300 (e.g., housing 206). The sensor is configured to convert the measurement of pressure to a corresponding electrical signal, which may include conversion of an analog to a digital signal. This sensor may be a digital sensor, digital pressure sensor or the like, some suitable examples of which are manufactured by Murata Manufacturing Co., Ltd.

The processing circuitry 308 is configured to receive the corresponding electrical signal from the sensor 310, and in response switchably connect the power source 312 to a load 322 including the heating element 316 and thereby power the heating element. The processing circuitry may be configured to process the corresponding electrical signal to determine an on/off condition, and may modulate switching connection of the power source to the load in proportion to the measurement of pressure produced by the sensor. In some examples, the control component 306 further includes a high-side load switch (LS) 324 between the first power-source terminal 318a and the heating element 316, or between the sensor and the load. In these examples, the processing circuitry may be configured to control the high-side LS to switchably connect the power source to the heating element. The high-side LS may also function as a safety feature in case there is a surge of current, if at all some components do short circuit or if the power source undergoes a solid electrode interphase.

As also shown, the aerosol delivery device 300 includes a micro pump 326 that may correspond to or include functionality of the micro pump 248. The micro pump is configured to deliver aerosol precursor composition from a reservoir (e.g., reservoir 220) to the heating element 316. In this regard, the aerosol delivery device may further include a liquid transport element 328 (e.g., liquid transport element 224) between and fluidly connecting the micro pump and the heating element. In some examples, the micro pump is a mechanical micro pump, and the mechanical micro pump is a diaphragm micro pump or a peristaltic micro pump. In other examples, the micro pump is a non-mechanical micro pump, and the non-mechanical micro pump is a valveless micro pump, a capillary micro pump or a chemically-powered pump. More particular examples of suitable micro pumps include the mp5-series and mp6-series micro pumps from Bartels Mikrotechnik GmbH of Dortmund, Germany.

In some examples, the liquid transport element 328 includes tubing between and fluidly connecting the reservoir and an inlet of the micro pump, and tubing between and fluidly connecting an outlet of the micro pump and the heating element 316. Examples of suitable tubing include flexible polymer tubing such as Tygon® tubing.

The aerosol delivery device 300 further includes a driver circuit 330 with a boost converter 332 coupled to and between the first power-source terminal 318a and the micro pump 326. One example of a suitable driver circuit is described in Microchip Technology, Inc., Application Note, AN2104—*Piezoelectric Micropump Driver Reference Design* (2016). The driver circuit is configured to drive the micro pump, with the boost converter being configured to step up voltage from the power source 312 to the micro pump to thereby power the micro pump. In some examples, this higher voltage is on the order of 250 volts at which the micro pump is configured to operate. The processing circuitry 308 is configured to control the driver circuit 330 to switchably drive the micro pump 326 to deliver the aerosol precursor composition to the heating element 316. And the processing circuitry is also configured to switchably connect the power source to the heating element independent of the boost converter and thereby power the heating element to vaporize components of the aerosol precursor composition.

In some examples, the processing circuitry 308 is configured to switchably drive the micro pump 326 to deliver the aerosol precursor composition once for a predetermined period per n>1 cycles of the power source 312 being switchably connected to the heating element 316. In some examples, the processing circuitry is configured switchably drive the micro pump 326 at an adjustable frequency that is directly related to a volume flow rate of aerosol precursor composition through the micro pump. Relatedly, in some examples, the processing circuitry is configured to control the boost converter 332 to step up the voltage from the power source to an adjustable higher voltage that is directly related to the volume flow rate of aerosol precursor composition through the micro pump.

In some examples, the control component 306 is further configured to receive an indication of a user-selected amount of aerosol precursor composition, such as via an appropriate input element as described above. The control component may further includes a communication interface 334 coupled to the processing circuitry 308 and configured to enable the aerosol delivery device 300 to establish wireless communication with a computing device configured to provide the indication of the user-selected amount of aerosol precursor composition. In these examples, the processing circuitry may cause the micro pump 326 to deliver the selectable amount of aerosol precursor composition to the heating element 316. This may be accomplished through control of the driver circuit 330 to switchably drive the micro pump at an adjustable frequency that causes delivery of the selectable amount of aerosol precursor composition. Or it may be accomplished through control the boost converter 332 to step up the voltage from the power source 312 to an adjustable higher voltage that causes delivery of the selectable amount of aerosol precursor composition.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device, comprising:
a housing enclosing a reservoir configured to retain an aerosol precursor composition;
a first power-source terminal configured to connect a power source to the aerosol delivery device;
a heating element configured to convert electricity to heat and thereby vaporize components of the aerosol precursor composition;
a switch coupled to and between the first power-source terminal and the heating element;
a micro pump arranged to be operable between the reservoir and the heating element to deliver aerosol precursor composition from the reservoir to the heating element;
a driver circuit including a boost converter coupled to and between the first power-source terminal and the micro pump, the driver circuit being configured to drive the micro pump via the boost converter; and
a control component including processing circuitry configured to switchably control the driver circuit to drive the micro pump to deliver the aerosol precursor composition to the heating element, the processing circuitry also being configured to switchably control the switch to connect the power source to the heating element independently of the driver circuit and thereby power the heating element independently of the boost converter to vaporize components of the aerosol precursor composition.

2. The aerosol delivery device of claim 1, wherein the boost converter is configured to step up voltage from the power source to the micro pump to thereby power the micro pump.

3. The aerosol delivery device of claim 2, wherein the processing circuitry is configured to switchably control the switch to connect the power source to the heating element independent of the boost converter.

4. The aerosol delivery device of claim 1, comprising:
a sensor configured to produce a measurement of pressure caused by airflow through at least a portion of the housing, and convert the measurement of pressure to a corresponding electrical signal,
wherein the processing circuitry being configured to switchably control the switch to connect the power source to the heating element includes being configured to receive the corresponding electrical signal and in response control the switch to connect the power source to the heating element.

5. The aerosol delivery device of claim 1, wherein the switch is a high-side load switch, and the processing circuitry being configured to switchably control the switch to connect the power source to the heating element includes being configured to switchably control the high-side load switch to connect the power source to the heating element.

6. The aerosol delivery device of claim 1, wherein the micro pump is a mechanical micro pump, and the mechanical micro pump is a diaphragm micro pump or a peristaltic micro pump.

7. The aerosol delivery device of claim 1, wherein the micro pump is a non-mechanical micro pump, and the non-mechanical micro pump is a valveless micro pump, a capillary micro pump or a chemically-powered pump.

8. The aerosol delivery device of claim 1, comprising a liquid transport element between and fluidly connecting the micro pump and the heating element.

9. The aerosol delivery device of claim 1, wherein the processing circuitry is configured to switchably drive the micro pump to deliver the aerosol precursor composition once for a predetermined period per n>1 cycles of the power source being switchably connected to the heating element via the switch.

10. The aerosol delivery device of claim 1, wherein the processing circuitry being configured to switchably control the driver circuit includes being configured to switchably control the driver circuit to drive the micro pump at an adjustable frequency that is directly related to a volume flow rate of aerosol precursor composition through the micro pump.

11. The aerosol delivery device of claim 1, wherein the boost converter is configured to step up voltage from the power source to the micro pump to thereby power the micro pump, and wherein the processing circuitry being configured to switchably control the driver circuit includes being configured to switchably control the boost converter to step up the voltage from the power source to an adjustable higher voltage that is directly related to a volume flow rate of aerosol precursor composition through the micro pump.

12. The aerosol delivery device of claim 1, wherein the boost converter is configured to step up voltage from the power source to the micro pump to thereby power the micro pump, wherein the control component is further configured to receive an indication of a user-selected amount of aerosol precursor composition, and wherein the processing circuitry being configured to switchably control the driver circuit includes being configured to switchably control the driver circuit to drive the micro pump at an adjustable frequency, or switchably control the boost converter to step up the voltage from the power source to an adjustable higher voltage, that causes the micro pump to deliver the selectable amount of aerosol precursor composition to the heating element.

13. The aerosol delivery device of claim 12, wherein the control component further includes a communication interface coupled to the processing circuitry and configured to enable the aerosol delivery device to establish wireless communication with a computing device configured to provide the indication of the user-selected amount of aerosol precursor composition.

14. The aerosol delivery device of claim 1, wherein the aerosol precursor composition comprises glycerin and nicotine.

15. The aerosol delivery device of claim 1, wherein the first power-source terminal and a second power-source terminal, the micro pump, the driver circuit and the control component are contained within the housing.

16. The aerosol delivery device of claim 1, wherein the housing is of a cartridge, the aerosol delivery device further comprises a control body with a second housing, and the first power-source terminal and a second power-source terminal, the micro pump, the driver circuit and the control component are contained within the second housing.

17. A control body for an aerosol delivery device, the control body comprising:

a housing enclosing a reservoir configured to retain an aerosol precursor composition;

a first power-source terminal configured to connect a power source to the control body;

heating-element terminals configured to connect a heating element to the control body, the heating element being configured to convert electricity to heat and thereby vaporize components of the aerosol precursor composition;

a switch coupled to and between the first power-source terminal and the heating element;

a micro-pump terminal configured to connect a micro pump to the control body, the micro pump being arranged to be operable between the reservoir and the heating element to deliver aerosol precursor composition from the reservoir to the heating element;

a driver circuit including a boost converter coupled to and between the first terminal and the micro pump, the driver circuit being configured to drive the micro pump via the boost converter; and a control component including processing circuitry configured to switchably control the driver circuit to drive the micro pump to deliver the aerosol precursor composition to the heating element, the processing circuitry also being configured to switchably control the switch to connect the power source to the heating element independently of the driver circuit and thereby power the heating element independently of the boost converter to vaporize components of the aerosol precursor composition.

18. The control body of claim 17, wherein the boost converter is configured to step up voltage from the power source to the micro pump to thereby power the micro pump.

19. The control body of claim 17, wherein the processing circuitry is configured to switchably control the switch to connect the power source to the heating element independent of the boost converter.

20. The control body of claim 17, comprising:

a sensor configured to produce a measurement of pressure caused by airflow through at least a portion of the housing, and convert the measurement of pressure to a corresponding electrical signal, wherein the processing circuitry being configured to switchably control the switch to connect the power source to the heating element includes being configured to receive the corresponding electrical signal and in response control the switch to connect the power source to the heating element.

21. The control body of claim 17, wherein the switch is a high-side load switch, and the processing circuitry being configured to switchably control the switch to connect the power source to the heating element includes being configured to switchably control the high-side load switch to connect the power source to the heating element.

22. The control body of claim 17, wherein the micro pump is a mechanical micro pump, and the mechanical micro pump is a diaphragm micro pump or a peristaltic micro pump.

23. The control body of claim 17, wherein the micro pump is a non-mechanical micro pump, and the non-mechanical micro pump is a valveless micro pump, a capillary micro pump or a chemically-powered pump.

24. The control body of claim 17, wherein the processing circuitry is configured to switchably drive the micro pump to deliver the aerosol precursor composition once for a predetermined period per n>1 cycles of the power source being switchably connected to the heating element via the switch.

25. The control body of claim 17, wherein the processing circuitry being configured to switchably control the driver circuit includes being configured to switchably control the driver circuit to drive the micro pump at an adjustable frequency that is directly related to a volume flow rate of aerosol precursor composition through the micro pump.

26. The control body of claim 17, wherein the boost converter is configured to step up voltage from the power source to the micro pump to thereby power the micro pump, and wherein the processing circuitry being configured to switchably control the driver circuit includes being configured to switchably control the boost converter to step up the voltage from the power source to an adjustable higher voltage that is directly related to a volume flow rate of aerosol precursor composition through the micro pump.

27. The control body of claim 17, wherein the boost converter is configured to step up voltage from the power source to the micro pump to thereby power the micro pump, wherein the control component is further configured to receive an indication of a user-selected amount of aerosol precursor composition, and wherein the processing circuitry being configured to switchably control the driver circuit includes being configured to switchably control the driver circuit to drive the micro pump at an adjustable frequency, or switchably control the boost converter to step up the voltage from the power source to an adjustable higher voltage, that causes the micro pump to deliver the selectable amount of aerosol precursor composition to the heating element.

28. The control body of claim 27, wherein the control component further includes a communication interface coupled to the processing circuitry and configured to enable the control body to establish wireless communication with a computing device configured to provide the indication of the user-selected amount of aerosol precursor composition.

\* \* \* \* \*